United States Patent [19]

Johnson

[11] Patent Number: 5,135,759

[45] Date of Patent: Aug. 4, 1992

[54] METHOD TO PRESELECT THE SEX OF OFFSPRING

[75] Inventor: Lawrence A. Johnson, Silver Spring, Md.

[73] Assignee: The United States of America as represented by the Secretary of Agriculture, Washington, D.C.

[21] Appl. No.: 692,958

[22] Filed: Apr. 26, 1991

Related U.S. Application Data

[63] Continuation of Ser. No. 349,669, May 10, 1989, abandoned.

[51] Int. Cl.$^5$ .............................................. A61K 35/52
[52] U.S. Cl. ...................................... 424/561; 436/63; 436/172; 435/2
[58] Field of Search ................... 436/63, 172; 424/561

[56] References Cited

U.S. PATENT DOCUMENTS

4,083,957  4/1978  Lang .................................... 424/105
4,191,749  3/1980  Bryant ................................ 424/105

FOREIGN PATENT DOCUMENTS

2145112  3/1985  United Kingdom .

OTHER PUBLICATIONS

Culling, Handbook of Histopathological & Histochemical Techniques, Butterworth & Co., London, 1974, p. 192.
L. A. Johnson, "Flow Sorting of Intact X and Y Chromosome-Bearing Mammalian Spermatozoa," Cytometry, Suppl. 2, p. 66 Abstract (1988).
J. C. Conover and R. B. L. Gwatkin, "Pre-Loading of Mouse Oocytes with DNA-Specific Fluorochrome (Hoechst 33342) Permits Rapid Detection of Sperm-Oocyte Fusion," J. Reprod. Fert. 82: 681-690 (1988).
L. A. Johnson and R. N. Clarke, "Flow Sorting of X and Y Chromosome-Bearing Mammalian Sperm: Activation and Pronuclear Development of Sorted Bull, Boar, and Ram Sperm Microinjected into Hamster Oocytes," Gamete Res. 21: (1988).
L. A. Johnson et al., "Flow Cytometry of X and Y Chromosome-Bearing Sperm for DNA Using an Improved Preparation Method and Staining with Hoechst 33342," Gamete Res. 17: 203-212 (1987).
R. E. Hinkley et al., "Rapid Visual Detection of Sperm-Egg Fusion Using the DNA-Specific Fluorochrome Hoechst 33342," Dev. Biol. 118: 148-154 (1986).
L. A. Johnson and D. Pinkel, "Modification of a Laser-Based Flow Cytometer for High-Resolution DNA Analysis of Mammalian Spermatozoa," Cytometry 7: 268-273 (1986).
L. A. Johnson, "Gender Preselection in Farm Animals," Research for Tomorrow, 1986 Yearbook of Agriculture, pp. 73-77 (1986).
W. M. Grogan et al., "DNA Analysis and Sorting of Viable Mouse Testis Cells," J. Histochem. Cytochem. 29: 738-746 (1981).
M. R. Loken, "Separation of Viable T and B Lymphocytes Using a Cytochemical Stain, Hoechst 33342," J. Histochem. Cytochem. 28: 36-39 (1980).

Primary Examiner—Douglas W. Robinson
Assistant Examiner—Jean C. Witz
Attorney, Agent, or Firm—M. Howard Silverstein; John D. Fado; Curtis P. Ribando

[57] ABSTRACT

Intact X and Y chromosome-bearing sperm populations of rabbits and swine were separated according to DNA content using a flow cytometer/cell sorter. Sperm viability was maintained by special staining techniques and by sorting and collecting the sperm in nutrient media. The sorted sperm were surgically inseminated into the uteri of rabbits or swine. Of the offspring born from does inseminated with the sorted population of X-bearing sperm, 94% were females. Of offspring born from does inseminated with sorted Y-bearing sperm from the same ejaculate, 81% were males.

26 Claims, No Drawings

5,135,759

METHOD TO PRESELECT THE SEX OF OFFSPRING

This application is a continuation of application Ser. No. 07/349,669, filed May 10, 1989, now abandoned.

BACKGROUND OF THE INVENTION

1. Field of the Invention

This invention relates to a method of preselecting the sex of offspring by sorting sperm into X and Y chromosome-bearing sperm based on differences in DNA content.

2. Description of the Prior Art

Gender of animal offspring is important to livestock producers. Because the dairy farmer has little use for most bull calves, the use of sexed semen to produce only females would make milk production more efficient. Swine farmers would produce pork more efficiently if they were able to market only female swine, because females grow faster than males.

In beef cattle and sheep breeds, the male grows at a faster rate than the female and hence is preferred for meat production.

In addition, the ability to specify male or female offspring should shorten the time required for genetic improvements, since desirable traits are often associated with one or the other parent. Planning the sex of cattle offspring is already practiced on a limited basis. This procedure consists of removing embryos from the cow, identifying their potential gender, and re-implanting only those of the desired gender. However, an ability to separate sperm into male-producing and female-producing groups before they are used for artificial insemination could enhance the overall value of offspring produced by embryo transfer.

Every living being has a set of paired chromosomes, which carry all the genetic material necessary to maintain life and also to propagate new life.

All but one pair of chromosomes are called autosomes and carry genes for all the characteristics of the body, such as skin, hair and eye color, mature size, and body characteristics. The remaining pair are called sex chromosomes. They carry the genetic material that specifies gender. One sex chromosome is called X, the other Y.

A sperm from the male or an egg from the female contains one of each pair of autosomes; in addition, in mammals the egg always contains an X chromosome, while the sperm always carries either an X or Y chromosome.

When a sperm and egg unite and the sperm carries the Y chromosome, the offspring is male (XY); however, if the sperm carries an X chromosome when it unites with the egg, the resulting offspring is female (XX).

The only established and measurable difference between X and Y sperm that is known and has been proved to be scientifically valid is their difference in deoxyribonucleic acid (DNA) content. The X chromosome is larger and contains slightly more DNA than does the Y chromosome. The difference in total DNA between X-bearing sperm and Y-bearing sperm is 3.4% in boar, 3.8% in bull, and 4.2% in ram sperm.

The amount of DNA in a sperm cell, as in most normal body cells, is stable. Therefore, the DNA content of individual sperm can be monitored and used to differentiate X- and Y-bearing sperm.

Since the difference in DNA mass in the sex chromosomes of most mammals is the only scientifically validated, measurable difference between X- and Y-bearing sperm, the chromosomal constitution [Moruzzi, J. Reprod. Fertil. 57: 319 (1979)] and/or measurement of DNA mass [Pinkel et al. (1), Science 218: 904 (1982); Pinkel et al. (2), Cytometry 3: 1 (1982); Johnson and Pinkel, Cytometry 7: 268 (1986); Johnson et al. (1), Gam. Res. 16: 1 (1987); Johnson et al. (2), Gam. Res. 17: 203 (1987)] are the only verifiable means other than fertility for determining the sex-producing capability of a population of sperm. The literature describes many physical, biochemical, and functional methods that have purportedly sexed sperm [Amann and Seidel, "Prospects for Sexing Mammalian Sperm," Colorado Assoc. Univ. Press, Boulder (1982)]; several of these methods have been tested for relative DNA content [Pinkel et al., J. Anim. Sci. 60: 1303 (1985); Johnson (1), Theriogenoloy 29: 265 (1988)]. However, no method has been proven in controlled experiments to actually affect the sex ratio of offspring.

Previous studies have demonstrated that the difference in DNA content between X and Y chromosome-bearing sperm can be repeatedly measured and the sperm sex ratio of a sample of semen predicted [Johnson and Pinkel, supra; Johnson et al. (1), supra; Johnson et al. (2), supra; Johnson (1), supra; Johnson (2), Cytometry, Suppl. 2: 66 (Abstract) (1988)]. Verifiable separation by sorting of X and Y sperm based on DNA content has been accomplished with the vole [Pinkel et al. (1), supra; Johnson, In "Beltsville Symposia in Agricultural Research X," P. C. Augustine, H. D. Danforth, & M. R. Bakst (eds.), Martinus Nijhoff, Boston, pp. 121–134 (1986)] and the chinchilla [(Johnson et al. (1), supra]. However, preparation procedures damaged DNA viability. The sorting of sperm nuclei from several mammalian (bull, boar, ram, vole, chincilla) species into separate X and Y chromosome-bearing populations at purities ranging from 92 to 99% has been accomplished [Johnson and Clarke, Gam. Res. 21: 335 (1988)]. Nuclear decondensation and pronuclear development was demonstrated in hamster eggs that had been microinjected with sorted X- or Y-bearing bull, boar, or ram sperm [Johnson and Clarke, supra].

SUMMARY OF THE INVENTION

It is an object of this invention to provide a method for sorting mammalian sperm into X and Y chromosome fractions based on DNA content.

It is a further object of this invention to teach a method of staining the DNA of mammalian sperm while maintaining viability of the sperm.

It is a further object of this invention to provide a sheath fluid adapted to be used in a cell-sorting apparatus while maintaining viability of sperm cells.

It is a further object of this invention to provide a collecting fluid capable of maintaining the viability of sorted sperm cells.

Other objects and advantages of this invention will become readily apparent from the ensuing description.

DETAILED DESCRIPTION OF THE INVENTION

I have now demonstrated the separation, by flow sorting, of intact, viable X and Y chromosome-bearing rabbit and swine sperm populations based on relative DNA content; surgical insemination of the sorted sperm into does; and the subsequent birth of sexed offspring with a phenotypic sex ratio consistent with predictions based on the relative DNA content of the sorted sperm populations.

A flow cytometer measures the amount of fluorescent light given off when the sperm, previously treated with a fluorescent dye, pass through a laser beam. The dye binds to the DNA. The fluorescent light is collected by an optical lens assembly; the signal is transported to a photomultiple tube, amplied, and analyzed by computer. Because the X chromosome contains more DNA than the Y chromosome, the female sperm (X) takes up more dye and gives off more fluorescent light than the male sperm (Y).

For small differences in DNA to be detected between X and Y, the sperm must pass single file through the laser beam, which measures the DNA content of individual sperm.

In orthogonal flow cytometry, a suspension of single cells stained with a fluorochrome is made to flow in a narrow stream intersecting an excitation source (laser beam). As single cells pass through the beam, optical detectors collect the emitted light, convert the light to electrical signals, and the electrical signals are analyzed by a multichannel analyzer. The data are displayed as multi- or single-parameter histograms, using number of cells and fluorescence per cell as the coordinates.

In order to use an orthogonal flow cytometric system to differentiate between X- and Y-bearing sperm DNA, a beveled sample injection tip and a second fluorescence detector in the forward position is required [Johnson and Pinkel, supra]. This paper is herein incorporated by reference. The modified system allows one to control the orientation of the flat ovoid sperm head as it passes the laser beam. Elimination of the unoriented sperm by electronic gating enhances precision. Typically, 80% of sperm nuclei (without tails) are properly oriented as they pass the laser beam.

In the modified Epics V flow cytometer/cell sorter, hydrodynamic forces exerted on the flat, ovoid mammalian sperm nuclei orient the nuclei in the plane of the sample stream as they exit the beveled injection tip. Fluorescent signals are collected simultaneously by 90 and 0 degree optical detectors, from the edge and flat side of the sperm nucleus, respectively. For sorting, the sample stream is broken into uniform droplets by an ultrasonic transducer. Droplets containing single sperm of the appropriate fluorescence intensity are given a charge and electrostatically deflected into collection vessels. The collected sperm nuclei then can be used for microinjection into eggs. Since the sperm nuclei have no tails, they cannot be used for normal insemination.

Accurate measurement of mammalian sperm DNA content using flow cytometry and cell sorting is difficult because the sperm nucleus is highly condensed and flat in shape, which makes stoichiometric staining difficult and causes stained nuclei to have a high index of refraction. These factors contribute to emission of fluorescence preferentially from the edge or thin plane of the sperm nucleus. In most flow cytometers and sorters, the direction of sample flow is orthogonal to the direction of propagation of the laser beam and the optical axes of the fluorescence detection. Consequently, fluorescence measurement is most accurate when the sperm fluorescence is excited and measured on an axis perpendicular to the plane of the sperm head [Pinkel et al. (2), supra]. At relatively low sample flow rates, hydrodynamics are used to orient tailless sperm so that DNA content can be measured precisly on 60 to 80% of the sperm passing in front of the laser beam. The modified Epics V system used in this study can measure the DNA content of tailless sperm from most species at the rate of 50 to 150 sperm per second [Johnson and Pinkel, supra].

Intact sperm (with tails), whether viable or nonviable, cannot be oriented as effectively as tailless sperm nuclei [Johnson (2), supra]. However, a 90-degree detector can be used to select the population of properly oriented intact sperm to be measured by the 0 degree detector. Since no hydrodynamic orientation is attempted, the sample flow rate can be much higher, which compensates somewhat for the fact that only 15 to 20% of intact sperm pass through the laser beam with proper orientation. In this invention, the overall flow rate was approximately 2500 intact sperm per second. The intact X- and Y-bearing sperm fractions were sorted simultaneously from the population of input sperm at a rate of 80–90 sperm of each type per second.

It is, of course, of critical importance to maintain high viability of the intact sperm during the sorting process and during storage after sorting but prior to insemination.

Of the factors involved in maintaining sperm viability, the method of staining, the sheath fluid, and the collecting fluid have been found to be especially important.

A nontoxic DNA stain must be selected. A preferred stain is Hoechst bisbenzimide H 33342 fluorochrome (Calbiochem-Behring Co., La Jolla, Calif.). To our knowledge, this fluorochrome is the only DNA binding dye that is nontoxic to sperm. Concentration of the fluorochrome must be minimal to avoid toxicity, and yet be sufficient to stain sperm uniformly and to detect the small differences in the DNA of X and Y sperm with minimal variation. A suitable concentration was found to be 5 $\mu$g/ml, but this may be varied from 4 to 5 $\mu$g/ml.

The sperm must be incubated with stain at sufficient temperature and time for staining to take place, but under mild enough conditions to preserve viability. Incubation for 1 hr at 35° C. was found to be acceptable, but ranges of 30° to 39° C. would also be effective. Incubation time has to be adjusted according to temperature; that is, 1.5 hr for 30° C.; 1 hr for 39° C.

Sheath fluid used in sorting cells must be electrically conductive and isotonic. A concentration of 10 mM phosphate buffered saline provided the necessary electrical properties, and 0.1% bovine serum albumin was added to enhance sperm viability by providing protein support for metabolism and viscosity for the sperm. The sheath fluid must be free of sugars and excess salts.

Dilution of sperm as occurs in sorting tends to reduce viability of the cells. To overcome this problem, sperm were collected in test egg yolk extender [Graham et al., J. Dairy Sci. 55: 372 (1972)] modified by adjusting the pH and adding a surfactant. Details of the composition of the extender are shown in Example 1. The surfactant is believed to enhance capacitation of the sperm prior to fertilization.

To confirm the DNA content and predict the sex of the offspring of surgically inseminated X or Y sorted sperm fractions, an aliquot of the sorted sperm was sonicated to remove the tails, stained, and the nuclei was reanalyzed for DNA content to predict the proportion of X and Y sperm.

Although the detailed description which follows uses the sorting of rabbit sperm as an example of this invention, it is expected that the sperm of most mammals could be effectively sorted by following these procedures. Those skilled in the art will recognize that minor modifications may be made in the procedure without departing from the spirit and scope of the invention.

Rabbit semen was collected, diluted, and stained with a fluorochrome dye. Sperm were sorted in a modified Epics V flow cytometer/cell sorter.

After being sorted, sperm were surgically inseminated into the uteri of rabbits.

The results obtained by surgical insemination of does with sorted intact sperm are presented in Table I. Recovery of ova 40 hr post-insemination indicated that stained sorted sperm, as well as unstained unsorted sperm, were capable of fertilizing rabbit ova in vivo.

Inseminations were also made to determine the comparability of predicted sex of offspring to phenotypic sex. As the data in Table II indicate, the predictability of the phenotypic sex based on DNA analysis of the separated intact sperm was very high. Reanalysis of the sorted Y population used for insemination indicated that 81% of the sperm were Y-bearing. The sex ratio of offspring from these inseminations was identical to that predicted. These values were significantly different from theoretical 50:50 sex rates ($P<0.003$). Reanalysis of the sorted X-bearing sperm population used for insemination indicated that 86% were X-bearing and 14% were Y-bearing sperm. The phenotypic sex of the offspring from these inseminations was 94% female, which was different from the theoretical 50:50 ($P<0.0003$).

Inseminations were made with sorted X and Y populations that were recombined (recombined X and Y group) immediately before insemination. The assumption was made that the proportions of X and Y in the recombined samples were equal (50:50). The phenotypic sex resulting from the inseminations was 57% female and 43% male (Table II) and was not significantly different from the theoretical (50:50) sex ratio ($P=0.40$).

TABLE I

| | Fertilizing Capacity of Flow-Sorted Rabbit Spermatozoa After Intrauterine Insemination of Does | | | |
|---|---|---|---|---|
| | Number of | | | |
| Treatment of Sperm | Does Inseminated | Ovulation Points | Eggs Recovered | Eggs Fertilized |
| Unsorted | 2 | 16 | 9 | 9 |
| Sorted | 6* | 59 | 46 | 39 |

*One doe accounted for 7 recovered and 7 unfertilized eggs.

kindling rate of near 80% and litter size of about six from does of this age and breed. However, the kindling rate across the three treatment groups averaged 28%, with an average litter size of 3.9. The cause of the apparent high rate of embryonic death is though to be due to the fluorochrome binding to the DNA and/or to the effect of the laser beam exciting the DNA bound fluorochrome. Earlier work has shown that sorted vole sperm nuclei that were microinjected into hamster eggs exhibited chromosome breakage in the developing sperm pronucleus [Libbus et al., Mut. Res. 182: 265 (1987)]. Those sperm had been sonicated, stained, sorted, and microinjected, a somewhat more rigorous treatment than the staining and sorting used in this study.

I have demonstrated that DNA can be used as a differentiating marker between X- and Y-bearing sperm, that DNA can be used to accurately predict the sex of offspring from separated X- and Y-bearing sperm populations, and that flow sorting is an effective means for separating viable X- and Y-bearing sperm populations suitable for production of offspring.

The following examples are intended only to further illustrate the invention and are not intended to limit the scope of the invention, which is defined by the claims.

EXAMPLE 1

Semen was collected from mixed breed mature bucks by use of an artificial vagina. Sperm concentration was determined with a hemocytometer. The semen was diluted with Tris buffer, pH 6.9, to a concentration of $10 \times 10^6$ per ml. Bisbenzimide H 33342 fluorochrome was added at a concentration of 5 µg/ml. The samples were incubated for 1 hr at 35° C. Intact sperm were sorted on a modified EPICS V flow cytometer/cell sorter. The stained intact sperm were excited in the ultraviolet (UV; 361 and 364 nm) lines of a 5-watt 90-5 Innova Argon-ion laser operating at 200 mW. Data were collected as 256-channel histograms. Sheath fluid was 10 mM phosphate-buffered saline (PBS) containing 0.1% bovine serum albumin (BSA). Sperm were sorted into a test egg yolk extender.

The composition of the extender was N-tris(hydroxymethyl)-methyl-2-amino ethane sulfonic acid, 2.16 g; tris hydroxymethyl aminomethane, 0.51 g; dextrose, 0.1 g; streptomycin sulfate, 0.13 g; penicillin G, 0.08 g; egg yolk, 12.5 ml; Equex STM (Nova Chemical Sales, Scituato, Mass.), 0.5%; and distilled water, 50 ml. This

TABLE II

| | Predicted and Actual Sex Ratios of Offspring After Intrauterine Insemination of Sorted X and Y Chromosome-Bearing Rabbit Sperm | | | | | | |
|---|---|---|---|---|---|---|---|
| | Number of Does | | Total No. of Young Born | Percentage and Numbers of Offspring | | | |
| | | | | Predicted | | Actual | |
| Treatment of Sperm | Inseminated | Kindling | | % Males | % Females | % Males (N) | % Females (N) |
| Sorted Y | 16 | 5 | 21 | 81 | 19 | 81 (17) | 19 (4) |
| Sorted X | 14 | 3 | 16 | 14 | 86 | 6 (1) | 94 (15) |
| Recombined X and Y | 17 | 5 | 14 | 50 | 50 | 43 (6) | 57 (8) |
| Total | 47 | 13 | 51 | — | — | 47 (24) | 53 (27) |

The phenotypic sex ratio of offspring born of does inseminated with either sorted X-bearing or sorted Y-bearing sperm was different ($P<0.0002$ for X and $P<0.001$ for Y) from the theoretical (50:50) sex ratio expected from untreated semen.

Embryonic mortality was significant in the does inseminated with sorted intact sperm. With a reasonably high fertilization rate (Table I), one would expect a mixture was centrifuged, and only the supernatant was used. The sorted sperm were concentrated by incubating at room temperature for 1 hr, after which the more dilute fraction was removed and the remainder was used for insemination 1 to 4 hr later.

EXAMPLE 2

Mature New Zealand White does were injected with 150 international units of human chorionic gonadotropin (HCG) to induce ovulation, which was expected to occur 10 hr later. Seven hours after treatment with HCG, the does were surgically prepared by injection with Ketamine hydrochloride containing acepromazine and anesthetized under halothane and oxygen. The uterus was exposed by midline incision, and 100 µl of sorted or unsorted sperm was placed into the lumen of the anterior tip of each uterine horn through a 21-gauge needle. Standard management practices were used in caring for the rabbits. These does were sacrificed 40 hr post-insemination; uteri were flushed and recovered eggs evaluated. All fertilized eggs recovered were classified as morula. The results of these experiments are shown in Table I.

EXAMPLE 3

Table II shows the results of inseminations made into the tip of the uterine horn: the number of does that kindled and the phenotypic sex of the offspring compared to the predicted sex. Predicted sex of offspring was based on reanalysis of sorted intact sperm to determine relative DNA content. For reanalysis, the sorted sperm was sonicated for 10 sec and centrifuged at 15,000 g, the supernatant was discarded, and the pellet was resuspended in 9 µM bisbenzimide H 33342. Phenotypic sex of the offspring was determined soon after birth and confirmed at later ages up to 10 weeks. Recombined X and Y is the sorted X and Y sperm populations recombined immediately before insemination.

EXAMPLE 4

Using the methods of Examples 1, 2, and 3, viable swine sperm was sorted into viable X and Y chromosome-bearing populations. Two litters (18 pigs) from surgically inseminated boar semen produced 88% females from X-sorted sperm and 67% males from Y-sorted sperm.

It is understood that the foregoing detailed description is given mainly by way of illustration and that modification and variation may be made therein without departure from the spirit and scope of the invention.

I claim:

1. A method for sorting intact, viable, mammalian sperm into X- and Y-chromosome-bearing populations based on DNA content, the method comprising:
    a) staining intact, viable sperm collected from a male mammal with a fluorescent dye capable of selectively staining DNA in living cells by incubating the sperm with the dye at a temperature in the range of about 30°-39° C. for a period of time sufficiently long for staining to take place uniformly but sufficiently short to preserve viability of the sperm;
    b) passing the sperm into an electrically conductive and isotonic viability-supporting sheath fluid to form a suspension of sperm which are caused to flow singly in a stream of sheath fluid;
    c) passing the sheath fluid containing the sperm before an excitation light source causing the stained DNA to fluoresce;
    d) passing the sheath fluid containing the sperm through both a means for detecting the fluorescence of the stained DNA and also a cell sorting means, the means for detecting fluorescence having at least two detectors arranged such that a first detector determines the orientation of sperm on the basis of magnitude of fluorescence and controls a second detector to measure the DNA content of sperm on the basis of magnitude of fluorescence of those sperm that have been determined to be in a preselected orientation;
    e) selecting by said cell sorting means the sperm having a DNA content corresponding to a desired chromosome which will produce a desired gender of offspring, and separating the selected sperm from nonselected sperm; and
    f) collecting the selected sperm in a viability-supporting collecting fluid.

2. The method of claim 1, wherein said mammal is a rabbit.

3. The method of claim 1, wherein said mammal is a swine.

4. The method of claim 1, wherein said mammal is a bovine.

5. The method of claim 1, wherein said dye is bisbenzimide H33342 fluorochrome.

6. The method of claim 1, wherein said incubation is at a temperature of about 39° C. for a period of about 1 hr.

7. The method of claim 1, wherein said incubation is at a temperature of about 35° C. for a period of about 1 hr.

8. The method of claim 1, wherein said incubation is at a temperature of about 30° C. for about 1.5 hr.

9. The method of claim 1, wherein said sheath fluid is phosphate-buffered saline solution, the solution also containing 0.1% bovine serum albumin to enhance sperm viability.

10. The method of claim 1, wherein said collecting fluid is modified test egg yolk extender.

11. The method of claim 1, wherein said sperm are hydrodynamically oriented in the flow of sheath fluid prior to being passed before said light source.

12. The method of claim 1, wherein said sperm are hydrodynamically oriented in the flow of sheath fluid by passing the fluid in a narrow stream through and out of a bevelled injection tip prior to being passed before said light source.

13. A method to preselect the sex of mammalian offspring comprising:
    a) sorting sperm according to the method of claim 1; and
    b) inseminating a female mammal of the same species as the male mammal with the selected sperm in the collecting fluid.

14. A method to preselect the sex of mammalian offspring comprising:
    a) sorting sperm according to the method of claim 1; and
    b) fertilizing an egg obtained from a female mammal of the same species as the male mammal with the selected sperm in the collecting fluid.

15. The method of claim 1, further comprising eliminating sperm which are not properly oriented with an electronic gating system before sorting by said cell sorting means.

16. The method of claim 1, wherein the flow of sperm through the cell sorting means is regulated by an ultrasonic transducer.

17. The method of claim 1, wherein said sperm are sorted on the basis of X- or Y-chromosome DNA content with about 90% efficiency.

18. The method of claim 1, wherein said sperm are hydrodynamically oriented in the flow of sheath fluid and sperm which are not properly oriented are eliminated by an electronic gating system prior to being passed before said light source.

19. A method to preselect the sex of mammalian offspring comprising:
a) staining intact, viable sperm collected from a male mammal with a fluorescent dye capable of selectively staining DNA in living cells by incubating sperm with the dye at a temperature in the range of about 30°–39° C. for a period of time sufficiently long for staining to take place uniformly but sufficiently short to preserve viability of the sperm;
b) passing the sperm into an electrically conductive and isotonic viability-supporting sheath fluid to form a suspension of sperm which are caused to flow singly in a stream of sheath fluid;
c) passing the sheath fluid containing the sperm before an excitation light source causing the stained DNA to fluoresce;
d) passing the sheath fluid containing the sperm through both a means for detecting the fluorescence of the stained DNA and also a cell sorting means to measure the DNA content of the sperm on the basis of magnitude of fluorescence of the sperm;
e) selecting by said cell sorting means the sperm having a DNA content corresponding to a desired chromosome which will produce the desired gender of offspring, and separating the selected sperm from nonselected sperm; and
f) collecting the selected sperm in a viability-supporting collecting fluid.

20. A method for preparing intact, viable, mammalian sperm for sorting into X- and Y-chromosome-bearing populations based on DNA content, the method comprising staining intact, viable sperm collected from a male mammal with a fluorescent dye capable of selectively staining DNA in living cells by incubating the sperm with the dye at a temperature in the range of about 30°–39° C. for a period of time sufficiently long for staining to take place uniformly but sufficiently short to preserve viability of the sperm.

21. The method of claim 20, wherein said mammal is a swine.

22. The method of claim 20, wherein said mammal is a bovine.

23. The method of claim 20, wherein said dye is bisbenzimide H33342 fluorochrome.

24. The method of claim 20, wherein said incubation is at a temperature of about 39° C. for a period of about 1 hr.

25. The method of claim 20, wherein said incubation is at a temperature of about 35° C. for a period of about 1 hr.

26. The method of claim 21, wherein said incubation is at a temperature of about 30° C. for about 1.5 hr.

* * * * *